United States Patent [19]

Säynäjäkangas

[11] Patent Number: 4,625,733

[45] Date of Patent: Dec. 2, 1986

[54] PROCEDURE AND MEANS FOR TELEMETRIC MEASURING OF HEARTBEAT AND ECG SIGNAL, USING A MAGNETIC PROXIMITY FIELD

[76] Inventor: Seppo Säynäjäkangas, Köykkyrintie 20, 90440 Kempele, Finland

[21] Appl. No.: 632,031

[22] Filed: Jul. 18, 1984

[30] Foreign Application Priority Data

Nov. 11, 1983 [FI] Finland .................................. 834152

[51] Int. Cl.$^4$ ............................................. A61B 5/02
[52] U.S. Cl. .................................. 128/687; 128/696; 128/903
[58] Field of Search ............... 128/696, 903, 690, 687, 128/904

[56] References Cited

U.S. PATENT DOCUMENTS

| | | |
|---|---|---|
| 3,212,496 | 10/1965 | Preston ................................ 128/903 |
| 3,218,638 | 11/1965 | Honig ................................... 128/903 |
| 3,949,388 | 4/1976 | Fuller .................................... 128/903 |
| 4,038,976 | 8/1977 | Hardy et al. ......................... 128/690 |
| 4,425,921 | 1/1984 | Fujisaki et al. ...................... 128/690 |

Primary Examiner—William E. Kamm
Attorney, Agent, or Firm—Martin Smolowitz

[57] ABSTRACT

A procedure and a means for telemetric measurement of heartbeat and ECG signal, according to the procedure a person's heartbeat or ECG signal being measured in a suitable part of the body and transmitted from a separate transmitter means to a separate receiver means. The telemetric data transfer is carried out, using the magnetic proximity field, by controlling magnet coils in the transmitter unit, with the heartbeat or ECG signal detected in the body and amplified, the magnetic field produced by the magnet coils being essentially multidimensional, and by detecting in the receiver the magnetic field with a coil structure having at least partially an equivalent directional pattern of the magnetic field.

7 Claims, 8 Drawing Figures

PROCEDURE AND MEANS FOR TELEMETRIC MEASURING OF HEARTBEAT AND ECG SIGNAL, USING A MAGNETIC PROXIMITY FIELD

BACKGROUND OF THE INVENTION

The present invention concerns a procedure and means for telemetric measurement of heartbeat and ECG signal, according to the procedure a person's heartbeat or ECG signal being measured from a suitable point on the body and transmitted from a separate transmitter means to a separate receiver means.

In top-level sports/athletics, in sports/athletics training and in fitness training, it is important to measure the heartbeat reliably and without break during a person's performance, and without disturbance of the measurement by the performance. Various types of wireless measuring instruments based on radio waves and on capacitive phenomena are known, in which there is used for instance a receiver to be carried on the wrist and a transmitter attached to a suitable point on the body.

Although designs based on these data transmitting modes mentioned are usable, the way of measuring employed by the procedure of the present invention affords a more reliable and simple way to perform telemetric measurements of heartbeat and/or ECG signals.

SUMMARY OF THE INVENTION

The procedure of the invention is mainly characterized in that telemetric data transfer takes place by using a magnetic proximity field generated in the transmitter unit and by controlling magnetic coils using a heartbeat or ECG signal detected in the body and amplified, the directional magnetic field produced by these magnetic coils being substantially multidimensional, and by detecting in the receiver the said magnetic field with a coil structure having at least partially a corresponding multidimensional magnetic field directional pattern.

According to the procedure, in a separate transmitter means there is measured the person's ECG signal or heartbeat from a suitable part of the body and this signal is amplified in a signal amplifier. With the ECG or heartbeat signal amplified to a suitable voltage level, there are controlled, through a power amplifier, three magnet coils mounted at right angles to each other with a.c. signals encoded in accordance with the heartbeat. This a.c. signal controlled through the coils generates in the ambience of the transmitter means a magnetic so-called proximity field simultaneously in a way characteristic of each coil. Hereby, the combined effect of the coils creates in the ambience of the transmitter an easy-to-measure, three-dimensional and nearly circularly symmetric magnetic field.

In the receiver there have in an equivalent way been disposed three separate coils placed at right angles to each other, for detecting the magnetic field produced around the transmitter. It is detected and possible in this way to receive the heartbeat transmission data reliably and without objectionable breaks in the transmission.

Other advantageous embodiments of the procedure of the invention are characterized by that which is stated in the claims presented further below.

The means of the invention, by the aid of which a person's heartbeat or ECG signal is measurable and transmittable from a separate transmitter means to a separate receiver means, is mainly characterized in that for accomplishing telemetric data transmission in the transmitter unit and in the receiver unit there have been used coil structures having a substantially multidimensional magnetic field directional pattern.

Other advantageous embodiments of the means of the invention are mainly characterized by that which is stated in the claims presented below.

With the described three-dimensional coil structures of the transmitter means there and receiver means is achieved through the combined effect of the structures a nearly spherically symmetric measurement in the ambience of the transmitter means, and therefore a highly reliable and break-free data transmission connection between the transmitter and receiver means. Apparatus according to the procedure described has also been found to operate exceedingly well in practice and to be applicable even in the most exacting sports disciplines, e.g. in swimming, hurdles and sprinting, cross-country running, orientation, skiing, etc. The measuring method based on the use of a magnetic field presented here is moreover one of the few measuring and data transmission methods working in water.

BRIEF DESCRIPTION OF THE DRAWINGS

The procedure and means of the invention shall be described in the following with the aid of certain advantageous embodiments and figures, referring to the attached drawings, wherein.

DESCRIPTION OF THE PREFERRED EMBODIMENT

Figure 1:
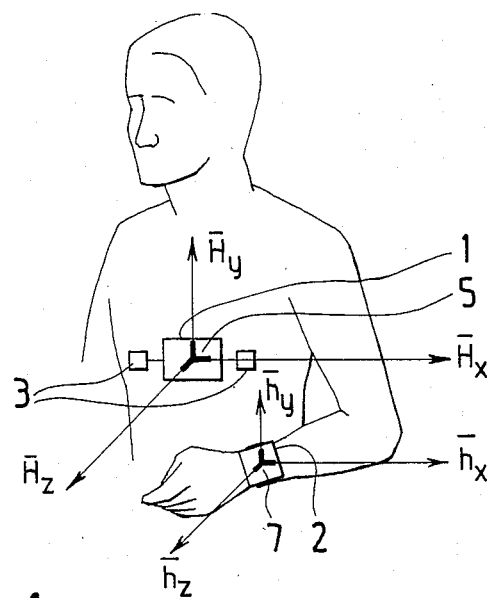
FIG. 1 presents telemetric heartbeat and ECG signal transmitter and receiver means and the magnet coils disposed in them in three directions at right angles to each other.

In FIG. 1, there is depicted a telemetric heartbeat transmitter means 1 carried on the breast of a person and a receiver means 2 carried on a wrist of the person. The ECG electrodes 3 disposed in the transmitter means are used to detect the person's ECG signal and to transform it electronically in the transmitter means 1 into an a.c. signal supplying current to the coils. The a.c. signal generates, as it runs through the coils, simultaneously in the ambience of each coil 5 equivalent three-dimensional magnetic fields $H_x$, $H_y$ and $H_z$.

In an equivalent three-dimensional manner, the three coils 7 in the receiver means 2, which coils are mounted at right angles to each other, measure in the ambience of the receiver means the magnetic fields $h_x$, $h_y$ and $h_z$. Independent of the changes in the relative positions of the coils 5 and 7, due to the person's body movements, it has been ensured by the design described that in nearly all positions at least one receiver coil 7 is able to detect the magnetic field generated by the coils 5 of the transmitter means 1.

Figure 2A:
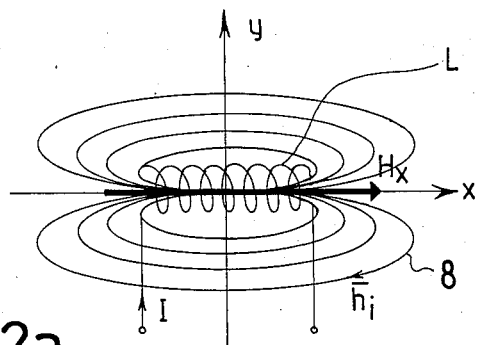
FIG. 2a shows, in x-y coordinates, the directional pattern of the magnetic field generated by a magnet coil.
Figure 2B:
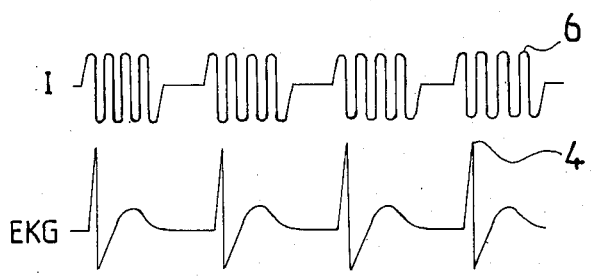
FIG. 2b shows the curve shape of the ECG signal and the wave form of the a.c. signal supplied into the transmitter coil, for generating an encoded magnetic field.

In FIG. 2a is depicted a magnet coil L, through which has been supplied, in accordance with FIG. 2b, an a.c. signal 6 encoded with the person's ECG signal 4. The a.c. signal 6 generates, as it passes through the coil L, a directional magnetic field $H_x$. The distribution of this field in the ambience of the coil L can be illustrated by equipotential flux lines 8. The magnetic field $h_i$ measurable point by point in the ambience of the coil L has always the direction of a fully closed flux line. It is well known that this field $h_i$ varies very strongly both as regards direction and field strength, and this impedes the detecting of a magnetic field created by only one magnet coil.

Figure 3:
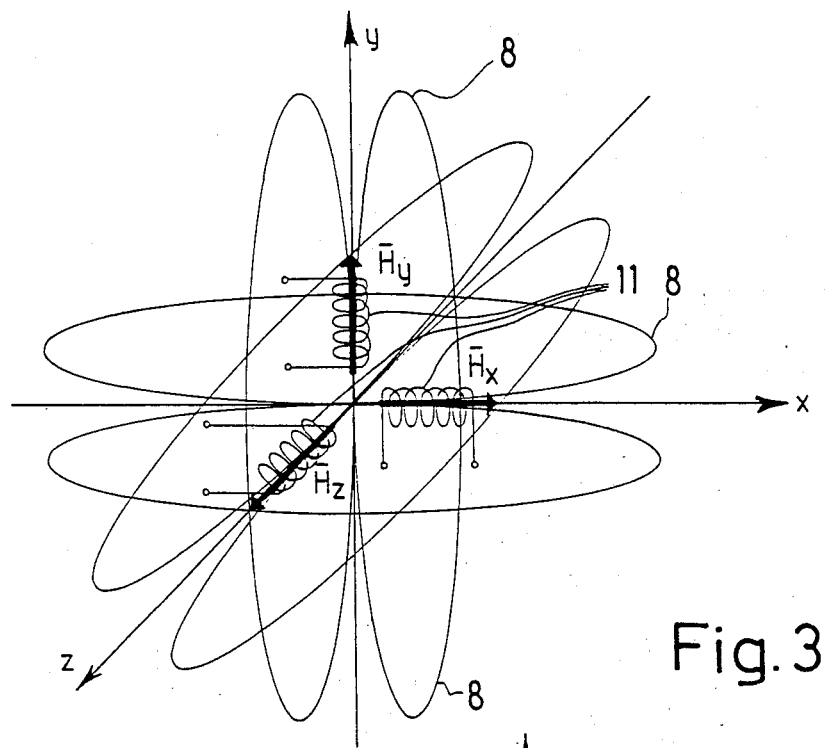
FIG. 3 shows, in x-y-z coordinates, the directional pattern of the magnetic field generated by three magnet coils.

In FIG. 3 have been shown, in x-y-z coordinates, the magnetic fields $H_x$, $H_y$ and $H_z$ of three magnet coils 11 placed at right angles to each other, the fields being produced with the a.c. signal 6. The directional pattern of the magnetic fields produced by the combined action of the coils 11 is symmetric in the x, y and z directions, but the field pattern contains shadow areas where even now the magnetic field varies very strongly regarding direction and intensity. By using for measurement of the magnetic field thus obtained, in the receiver means, a coil structure which likewise measures the magnetic field in three mutually perpendicular directions, one achieves by the joint effect of the structures described between the transmitter means 1 and the receiver means 2 a measuring procedure which operates almost with spherical symmetry from the viewpoint of the transmitter means 1.

Figure 4:
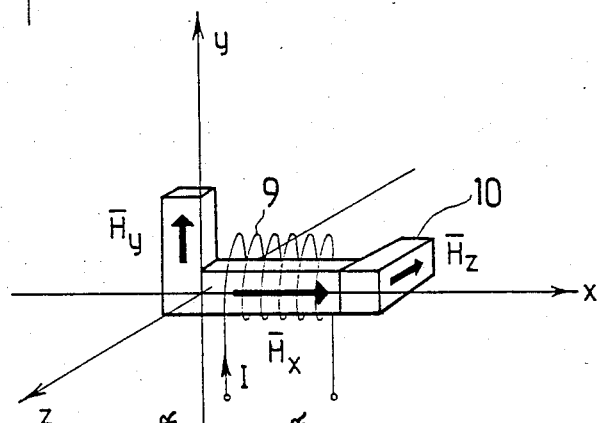
FIG. 4 shows, in x-y-z coordinates, the magnetic fields generated by a coil provided with a three-dimensional ferrite core.

In FIG. 4 is depicted another embodiment of the means of the invention, having one coil winding 9 which has been provided with three mutually perpendicular sections of ferrite coil 10, the magnetic field vectors produced by them being $H_x$, $H_y$ and $H_z$.

An a.c. signal 6 introduced in a coil winding 9 of this kind produces in the ambience of the coil winding a magnetic field which is measurable in all x, y and z directions. One may by the design just described replace three separate windings 11 as shown by FIG. 3 both in the transmitter means 1 and in the receiver means 2 and thereby achieve a similar, nearly spherically symmetric measuring method.

Figure 5:
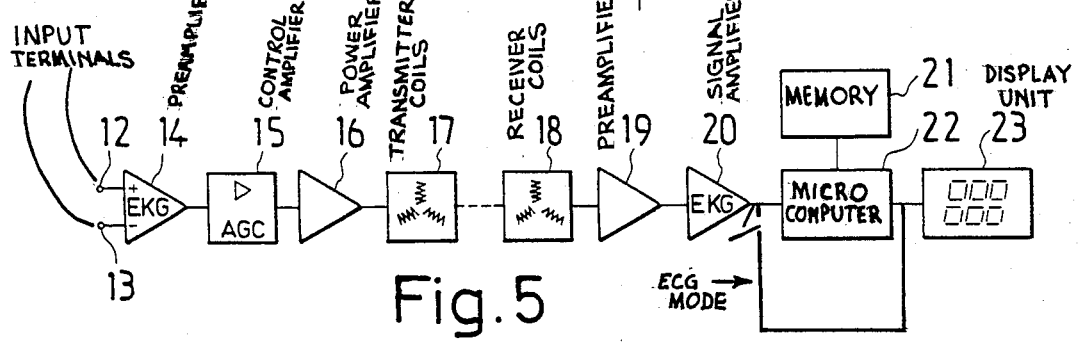
FIG. 5 presents in the form of a block diagram the circuitry of a transmitter and receiver means according to the invention in a heartbeat and ECG signal measuring means, illustrating means of effecting alternative mode of operation for ECG.

The electrodes 3 of the heartbeat and ECG signal measuring means have in FIG. 5 been connected directly to the differential input terminals 12 and 13 of an ECG preamplifier 14 of transmitter means 1. The ECG cardiac signal put out by the preamplifier 14 is amplified in the AGC (automatic gain control) amplifier 15. By this AGC amplifier is controlled a power amplifier 16, in which the a.c. signal controlling the coil windings 17 is produced. The magnetic field detected by the receiver coils 18 is amplified in a sensitive preamplifier 19, whereupon the signal is carried to a signal amplifier 20. From the signal amplifier 20, the signal is carried to processing by a microcomputer 22. The microcomputer 22 records in the semiconductor memory 21 the ECG and heartbeat data which it calculates in the measuring step. In the measuring step, the computer reads the ECG and heartbeat data and sends them as output to a liquid crystal display 23 of the receiver means 2.

Figure 6:
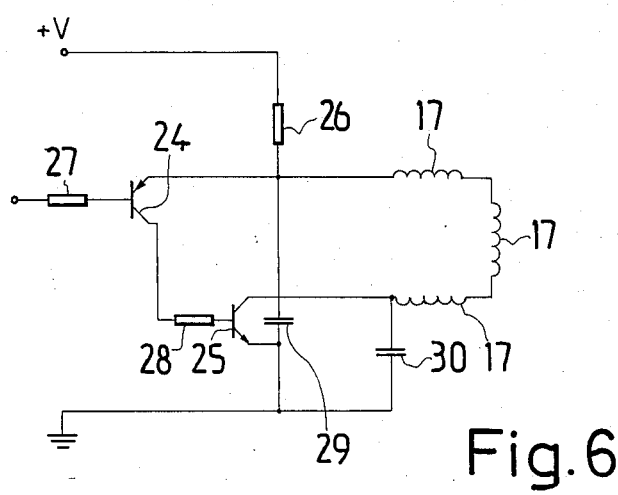
FIG. 6 is a circuit diagram of the power amplifier of the transmitter means and the transmitting coils coupled to it.

FIG. 6 shows the circuit diagram f the output stage of the transmitter means 1 and the manner in which the transmitting coils 5 are coupled to it.

The transmitting coils 17 are fed by the power stage with a sinusoidal a.c. signal 6, which generates a correspondingly alternating magnetic field 8 in the ambience of the transmitting coils 17.

Transistors 24,25 drive the transmitting coils 17 with a momentarily large current to cause the alternating magnetic field 8. Resistors 27,28 limit the base currents of the transistors 24,25. Capacitor 29 is used to store the necessary energy for each output burst and it is loaded through the resistor 26 from the supply voltage V+ during the time interval between consequent output bursts. Capacitor 30 together with the transmitting coils 17 form a LC− circuit, the resonant frequency of which is determined by the total inductance of the transmitting coils 17 and the capacitance value of the capacitor 30.

Figure 7:
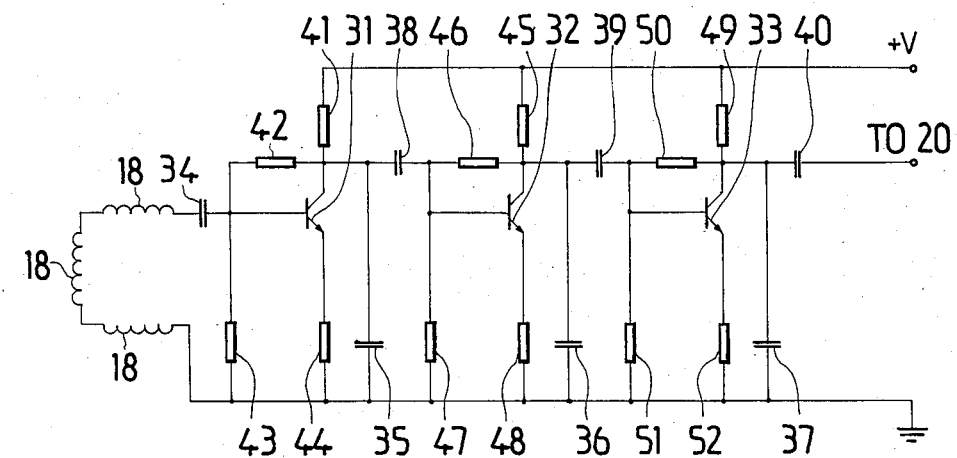
FIG. 7 is a circuit diagram of the preamplifier stage of the receiver means and the receiving coils coupled to it.

FIG. 7 shows the coupling of the receiving coils 18 to the preamplifier stage 19 shown in FIG. 5, wherein the magnetic field 8 detected by the receiving coils 18 is amplified to a sufficient voltage level to be put into the following pulse amplifier 20 (FIG. 5). The a.c. signal amplified by the pulse amplifier 20 is detected and further amplified onto a voltage level required by the microcomputer 22 of the receiving means 2.

The preamplifier stage of FIG. 7 consists of three cascaded transistor stages 31,32,33. Resistors 41,42,43,44; 45,46, 47,48 and 49,50,51,52 determine the gain and the d.c. bias voltages of each transistor stage. Capacitors 43,38,39,40 determine the lower corner frequency of the preamplifier. The higher corner frequency is determined by the integrating capacitors 35,36,37.

It is obvious to a person skilled in the art that different embodiments of the invention are not confined merely to the example presented above, and that they may instead vary within the scope of the claims presented below.

I claim:

1. A method for telemetric measurement of heartbeat signals whereby a person's heartbeat signal is measured from a suitable part of the body and the signal generated is transmitted from a transmitter to a receiver by telemetric data transmission comprising the steps of:
   (a) applying electrodes attached to the transmitter against a person's skin for detecting a heartbeat signal in said person's body:
   (b) amplifying the detected heartbeat signal, through amplifier means and generating a periodic low frequency signal dependent upon the detected and amplified heartbeat signal:
   (c) generating a periodic three-dimensional low frequency magnetic proximity field by feeding said low frequency periodic signal to three mutually perpendicular magnetic coils provided in the transmitter.
   (d) detecting by means of an inductive coupling, said three dimensional magnetic field with a receiver having a magnetic coil structure similar to that of said transmitter;
   (e) amplifying the signal received as induced in said receiver coils by a magnetic field generated by said transmitter coils;

(f) converting the received and amplified signal by known means to computer readable data;

(g) calculating the heartbeat value from said computer readable data by means of a computer interfaced with said receiving; and (h) displaying the heartbeat value on means interfaced with said computer.

2. A method of telemetric measurement according to claim 1, comprising the steps of: amplifying the heartbeat signal and encoding such signal with an a.c. signal to control the three magnetic coils of the transmitter.

3. A telemetric measuring apparatus for measuring a person's heartbeat signal being transmitted from a separate transmitter to a separate receiver comprising: electrodes for detection of the heartbeat signal, said electrodes being connected to said transmitter for attachment to a person's body; said transmitter including amplifier means for amplifying the detected heartbeat signal and three mutually perpendicular magnetic coils a common LC-circuit for controlling generation of a periodic three-dimensional magnetic field in response to said amplified signal; said receiver including a magnetic coil structure essentially similar to the coil structure in the transmitter for detecting the periodic magnetic field generated by said transmitter coil structures in response to the heartbeat signal, an amplifier for amplifying the detected heartbeat signal, and a digital signal processing means including computer means interfaced with said receiver for receiving said signal and processing same on through to display means in said receiver to display a heartbeat value thereon.

4. A telemetric measuring apparatus according to claim 3, wherein the coil structure of the transmitter and the receiver includes one coil winding which has been provided with three mutually perpendicular ferrite core elements.

5. A telemetric measuring apparatus according to claim 3, wherein said transmitter includes signal amplifier means for amplifying the heartbeat signal, and said receiver includes amplifier means for amplifying the magnetic field detection signal.

6. A telemetric measuring apparatus for measuring a person's ECG signal according to claim 3, whereby said signal is measured from a suitable part of the body being transmitted from a separate transmitter to a separate receiver, including electrodes for detection of the ECG signal, said electrodies being connected to said transmitter for attachment to a person's body; said transmitter including amplifier means for amplifying the detected ECG signal and three mutually perpendicular magnetic coils a common LC-circuit for controlling generation of a periodic three-dimensional magnetic field in response to said amplified signals; said receiver including a magnetic coil structure essentially similar to the coil structure in the transmitter, for detecting the periodic magnetic field generated by said transmitter coil structure in response to the ECG signal, an amplifier for amplifying the detected ECG signal, and a display means for displaying the amplified ECG signal.

7. A method for telemetric measurements of ECG signals whereby a person's ECG signal is measured from a suitable part of the body and the signal generated is transmitted from a transmitter to a separate receiver by telemetric data transmission comprising the steps of:

(a) applying electrodes attached to the transmitter against a person's skin for detecting an ECG signal in said person's body;

(b) amplifying the detected ECG signal, through amplifier means and generating a periodic low frequency signal dependent upon the detected and amplified ECG signal;

(c) generating a periodic three-dimensional low frequency magnetic proximity field by feeding said low frequency periodic signal to three mutually perpendicular magnetic coils provided in the transmitter;

(d) detecting by means of an inductive coupling, said three-dimensional magnetic field with a receiver having a magnetic coil structure similar to that of said transmitter;

(e) amplifying the signal received as induced in said receiver coils by a magnetic field generated by said transmitter coils; and (f) displaying the amplified ECG signal on display means interfaced with said receiver.

* * * * *